(12) United States Patent
Zal

(10) Patent No.: US 9,663,761 B2
(45) Date of Patent: May 30, 2017

(54) USE OF ANNELID HAEMOGLOBIN FOR MAINTAINING STEM CELLS IN THE UNDIFFERENTIATED STATE

(75) Inventor: Franck Zal, Ploujean-Morlaix (FR)

(73) Assignee: HEMARINA, Morlaix (FR)

(*) Notice: Subject to any disclaimer, the term of this patent is extended or adjusted under 35 U.S.C. 154(b) by 208 days.

(21) Appl. No.: 14/240,845

(22) PCT Filed: Aug. 23, 2012

(86) PCT No.: PCT/FR2012/051925
§ 371 (c)(1),
(2), (4) Date: Feb. 25, 2014

(87) PCT Pub. No.: WO2013/030496
PCT Pub. Date: Mar. 7, 2013

(65) Prior Publication Data
US 2014/0220683 A1 Aug. 7, 2014

(30) Foreign Application Priority Data
Aug. 26, 2011 (FR) ..................................... 11 57567

(51) Int. Cl.
*C12N 5/074* (2010.01)
*A01N 1/02* (2006.01)
*C12N 5/071* (2010.01)

(52) U.S. Cl.
CPC ......... *C12N 5/0607* (2013.01); *A01N 1/0226* (2013.01); *C12N 5/063* (2013.01); *C12N 5/0629* (2013.01); *C12N 2501/998* (2013.01)

(58) Field of Classification Search
None
See application file for complete search history.

(56) References Cited

U.S. PATENT DOCUMENTS 5,955,257 A * 9/1999 Burger et al. ..................... 435/2
2010/0209902 A1 8/2010 Zal et al.

FOREIGN PATENT DOCUMENTS

| FR | 2 919 785 | 2/2009 | |
| FR | WO 2010128159 A1 * | 11/2010 | ........... A01N 1/0226 |
| WO | 2008/143884 | 11/2008 | |
| WO | WO 2010128159 A1 * | 11/2010 | |

OTHER PUBLICATIONS

Mannello et al. "Concise Review: No Breakthroughs for Human Mesenchymal and Embryonic Stem Cell Culture: Conditioned Medium, Feeder Layer, or Feeder-Free; Medium with Fetal Calf Serum, Human Serum, or Enriched Plasma; Serum-Free, Serum Replacement Nonconditioned Medium, or Ad Hoc Formula? All That Glitters is Not Gold!." Stem Cells 25(7): 1603-1609.*
Kim et al. "Maintenance of an undifferentiated state of human induced pluripotent stem cells through migration-dependent regulation of the balance between cell-cell and cell-substrate interactions" Journal of Bioscience and Bioengineering 119(6): 617-622, 2015.*
Magnusson et al. "Expansion on Stromal Cells Preserves the Undifferentiated State of Human Hematopoietic Stem Cells Despite Compromised Reconstitution Ability" PLOS ONE 8(1): e53912, 2013.*
International Search Report dated Oct. 17, 2012, corresponding to PCT/FR2012/051925.
Hsin-Fu Chen, et al.; "Hypoxic Culture Maintains Self-Renewal and Enhances Embryoid Body Formation of Human Embryonic Stem Cells"; vol. 16, No. 9, Sep. 2010; pp. 2901-2913 (Abstract Only).

* cited by examiner

*Primary Examiner* — Emily Cordas
(74) *Attorney, Agent, or Firm* — Young & Thompson

(57) ABSTRACT

A method for maintaining stem cells in the undifferentiated state by mixing the stem cells with at least one extracellular hemoglobin, globin or globin protomer from annelids.

17 Claims, 2 Drawing Sheets

USE OF ANNELID HAEMOGLOBIN FOR MAINTAINING STEM CELLS IN THE UNDIFFERENTIATED STATE

FIELD OF THE INVENTION

The present invention relates to the use of at least one extracellular hemoglobin, globin or globin protomer from annelids, for maintaining stem cells in the undifferentiated state.

BACKGROUND OF THE INVENTION

Stem cells today constitute a valuable therapeutic potential, in particular from the point of view of regenerative or therapeutic medicine. They group together various specific cell categories:
- adult stem cells: the first discovered were blood cells. They are widely used after chemotherapy, which destroys the bone marrow cells. An autologous graft (from the patient himself) makes it possible to produce blood cells more rapidly, without the risk of rejection. All tissues and all organs contain adult stem cells, but they are rare and difficult to purify;
- perinatal stem cells: they are contained in the umbilical cord, the placenta and the blood which is contained therein. Mention may be made of blood stem cells, which can be used for grafts, but must be compatible from an immunological point of view;
- mesenchymal stem cells: they can be both perinatal (contained in the umbilical cord and the placenta) and adult. They then originate mainly from the bone marrow and the adipose tissue;
- embryonic stem cells: these cells originate from "surplus" embryos, and are particularly advantageous for research since they are completely undifferentiated and can become specialized for all the human tissues. There are of course medical applications (compensating for the deficiencies of certain organs), but also pharmacological applications; and finally
- reprogrammed cells, also called "induced pluripotent stem cells" or "iPS" cells: by introducing 4 genes capable of completely reprogramming it, researchers have transformed a differentiated adult skin cell into a pluripotent stem cell. This technique has been used on mice suffering from sickle-cell anemia. The diseased red blood cells were corrected by gene therapy, dedifferentiated, and then reinjected into the mouse. A cure could thus be obtained using cells from the sick mouse itself.

In order to be able to use these stem cells in therapy and to develop applications thereof, it is necessary to preserve them, for the desired time, in the undifferentiated state. This is because said cells differentiate very rapidly into a given cell type, which makes them unusable for (re)directing their differentiation toward a different cell type, or for carrying out fundamental research studies on these cells.

There is therefore a need to maintain stem cells, in particular animal stem cells, more particularly human stem cells, in the undifferentiated state in order to trigger the differentiation process at the desired moment.

The inventors have now discovered that, surprisingly, the extracellular hemoglobin from annelids, when it is added to stem cells, in particular human stem cells, makes it possible to maintain the latter in the undifferentiated state, while at the same time preserving their viability.

SUMMARY OF THE INVENTION

The present invention thus relates to the use of at least one extracellular hemoglobin, globin or globin protomer from annelids, for maintaining stem cells in the undifferentiated state. The stem cells may be murine or human, they are preferably human.

The extracellular hemoglobin from annelids is present in the three classes of annelids: the polychaetes, the oligochaetes and the achaetes. Reference is made to extracellular hemoglobin because it is not naturally contained in a cell, and can therefore circulate freely in the blood stream without chemical modification to stabilize it or make it functional.

The extracellular hemoglobin from annelids is a giant biopolymer with a molecular weight of between 2000 and 4000 kDa, consisting of approximately 200 polypeptide chains of between 4 and 12 different types which are generally grouped into two categories.

The first category, with 144 to 192 components, groups together the "functional" polypeptide chains which bear an active site of heme type, and are capable of reversibly binding oxygen; these are chains of globin type, the weights of which are between 15 and 18 kDa and which are very similar to the α- and β-type chains of vertebrates.

The second category, with 36 to 42 components, groups together the "structural" or "linker" polypeptide chains which have few or no active sites but enable the assembly of the subunits called one-twelfth subunits or protomers.

Each hemoglobin molecule consists of two superposed hexagons which have been named hexagonal bilayer, and each hexagon is itself formed by the assembly of six subunits (or "one-twelfth subunits" or "protomers") in the form of a drop of water. The native molecule is made up of twelve of these subunits (dodecamer or protomer). Each subunit has a molecular weight of between 200 and 250 kDa, and constitutes the functional unit of the native molecule.

DETAILED DESCRIPTION OF THE INVENTION

Preferably, the extracellular hemoglobin from annelids is chosen from the extracellular hemoglobins from polychaete annelids, preferably from the extracellular hemoglobins from the family Arenicolidae and the extracellular hemoglobins from the family Nereididae. Even more preferentially, the extracellular hemoglobin from annelids is chosen from the extracellular hemoglobin from *Arenicola* sp and the extracellular hemoglobin from *Nereis* sp, more preferentially the extracellular hemoglobin from *Arenicola marina* or from *Nereis virens*.

According to the invention, the globin protomer of the extracellular hemoglobin from annelids constitutes the functional unit of native hemoglobin, as indicated above. Finally, the globin chain of the extracellular hemoglobin from annelids can in particular be chosen from the Ax and/or Bx type globin chains of extracellular hemoglobin from annelids.

The extracellular hemoglobin from annelids and globin protomers thereof have intrinsic superoxide dismutase (SOD) activity, and consequently require no antioxidant in order to function, contrary to the use of a mammalian hemoglobin, for which the antioxidant molecules are contained in the red blood cell and are not bonded to the hemoglobin. Furthermore, the extracellular hemoglobin from annelids, globin protomers thereof and/or globins thereof do not require a cofactor in order to function, contrary to mammalian hemoglobin, in particular human hemoglobin. Finally, the extracellular hemoglobin from annelids, globin protomers thereof and/or globins thereof do not possess blood typing; they make it possible to avoid any problem of immunological reaction.

The extracellular hemoglobin from annelids, globin protomers thereof and/or globins thereof may be native or recombinant.

According to the invention, the extracellular hemoglobin, globin or globin protomer from annelids is preferably present in a composition comprising a buffer solution. In this case, the extracellular hemoglobin, globin or globin protomer from annelids is preferably present in the composition at a concentration of between 0.001 and 10 mg/ml, preferably between 0.20 and 1.50 mg/ml and preferably between 0.25 and 1.25 mg/ml.

Said buffer solution creates an appropriate saline environment for the hemoglobin, protomers thereof and globins thereof, and thus enables the quaternary structure and therefore the functionality of this molecule to be maintained. By virtue of the buffer solution, the hemoglobin, protomers thereof and globins thereof are capable of performing their oxygenation function.

The buffer solution according to the invention is an aqueous solution comprising salts, preferably chloride, sodium, calcium, magnesium and potassium ions, and confers on the composition according to the invention a pH of between 6.5 and 7.6; its formulation is similar to that of a physiologically injectable liquid. Under these conditions, the extracellular hemoglobin from annelids, globin protomers thereof and globins thereof remain functional.

In the present description, the pH is understood to be at ambient temperature (25° C.), unless otherwise mentioned.

Preferably, the buffer solution is an aqueous solution comprising sodium chloride, calcium chloride, magnesium chloride, potassium chloride and also sodium gluconate and sodium acetate, and has a pH of between 6.5 and 7.6, preferably equal to 7.1±0.5, preferably of approximately 7.35. More preferentially, the buffer solution is an aqueous solution comprising 90 mM of NaCl, 23 mM of Na-gluconate, 2.5 mM of $CaCl_2$, 27 mM of Na-acetate, 1.5 mM of $MgCl_2$, 5 mM of KCl, and at a pH of 7.1±0.5, which can contain between 0 and 100 mM of antioxidant of ascorbic acid and/or reduced glutathione type.

Preferably, the stem cells maintained in the undifferentiated state according to the invention are chosen from induced pluripotent stem cells (iPS cells), embryonic stem cells, perinatal stem cells, adult stem cells and mesenchymal stem cells. Said stem cells are preferably animal, even more preferentially human.

The present invention also relates to a method for preserving stem cells in the undifferentiated state, preferably human stem cells, comprising a step of mixing stem cells with a buffer solution comprising at least one extracellular hemoglobin, globin or globin protomer from annelids. The extracellular hemoglobin, globin and globin protomer from annelids are preferably as described above.

The extracellular hemoglobin from annelids according to the invention, preferably present in a buffer solution, can be added directly to the stem cells or to the medium containing them. Preferably, said stem cells are maintained for a period of approximately 1 to 15 days in contact with the extracellular hemoglobin from annelids, or even for longer depending on the application envisioned. Next, if the extracellular hemoglobin from annelids is removed, for example by filtration or pipetting, the stem cells can again differentiate.

The invention is described in greater detail in the following examples. These examples are given for the purposes of illustration only, and are not limiting.

The illustrative figures are the following:

EXAMPLES

Materials and Methods

Active Agent

The extracellular hemoglobin from annelids, in this case from *Nereis virens*, in solution in a buffer solution comprising 90 mM of NaCl, 23 mM of Na-gluconate, 2.5 mM of $CaCl_2$, 27 mM of Na-acetate, 1.5 mM of $MgCl_2$, 5 mM of KCl, and at a pH of 7.1±0.5, which can contain between 0 and 100 mM of antioxidant of ascorbic acid and/or reduced glutathione type, is used at the tested concentrations of 0.25, 0.75 and 1.25 mg/ml. This hemoglobin is available under the reference Hemarina-M201 from the company Hemarina.

CFE Clonogenicity Test (2D)

Principle: The CFE clonogenic efficiency test makes it possible to evaluate the frequency of keratinocytes capable of generating a cell clone within a given population. It is considered that a strong clonogenic potential is associated with stem/progenitor cells, whereas differentiated keratinocytes lose this potentiality. This culture test consists in seeding keratinocytes at low density (from 100 to 1000 cells per dish), so as to obtain well-individualized clones, which can be easily counted and are easy to distinguish from a qualitative point of view. The culturing is carried out in medium containing serum on a feeder layer of irradiated fibroblasts.

Protocol: The extracellular hemoglobin from *Nereis virens* (Hemarina-M201) was tested independently on various cell populations:

Test on a bank of preamplified run-of-the-mill keratinocytes: immediately after thawing, the cells were seeded in a proportion of 100 cells per Petri dish under CFE conditions in the presence of Hemarina-M201 or the absence of the latter (control) in the culture medium.

Test on cell populations freshly extracted from a breast skin plasty and subsequently enriched in or depleted of epidermal stem and progenitor cells: On D0, the cells were seeded in a proportion of 1000 cells per Petri dish under CFE conditions in the presence or absence (control) of Hemarina-M201 in the culture medium.

On D3 and D8 of culture, the media were changed in the presence or absence (control) of Hemarina-M201 in the culture medium. The culture was continued up to D13 and then stopped and fixed and the cell clones were stained and analyzed. Each condition was tested in triplicate.

Results

Figure 2:
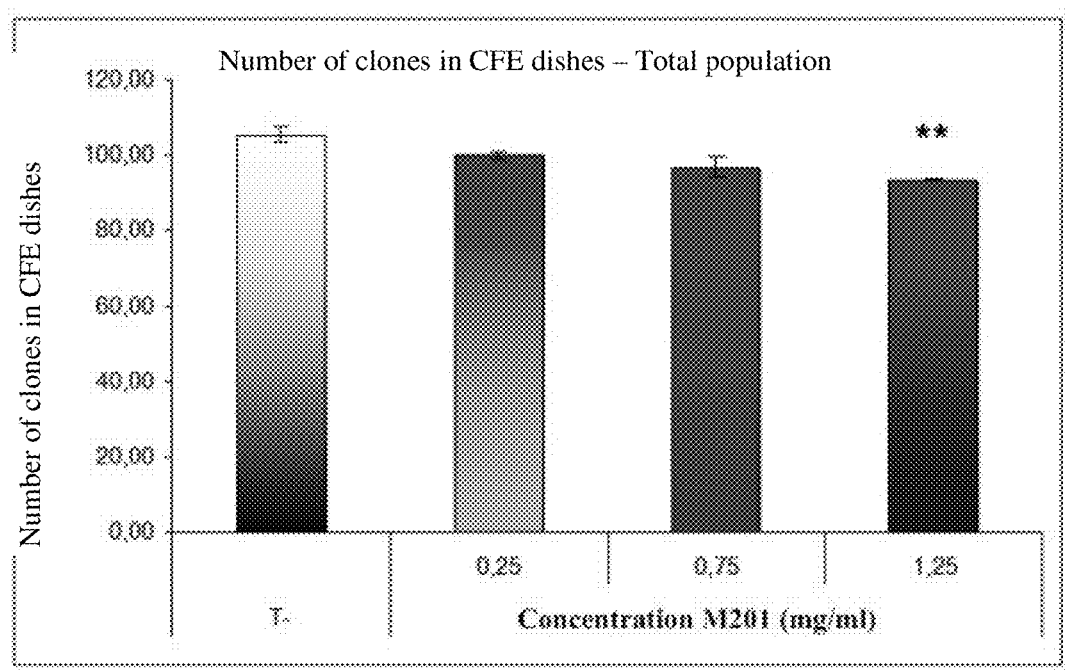
FIG. 2: Results of counting the number of clones present in the CFE dishes after fixing and staining of the clones obtained after 13 days of culture for the population enriched in stem cells. The results are the means of the triplicates per condition.

Evaluation of Hemarina-M201 on a Population of Run-of-the-Mill Keratinocytes from Two Banks:

For the first bank, the number of clones present in the CFE dishes after 13 days of culture is not significantly different between the control, Hemarina-M201 at 0.25 mg/ml, Hemarina-M201 at 0.75 mg/ml and Hemarina-M201 at 1.25 mg/ml conditions (FIG. 2). Hemarina-M201 does not therefore influence the viability of said clones.

Figure 1:
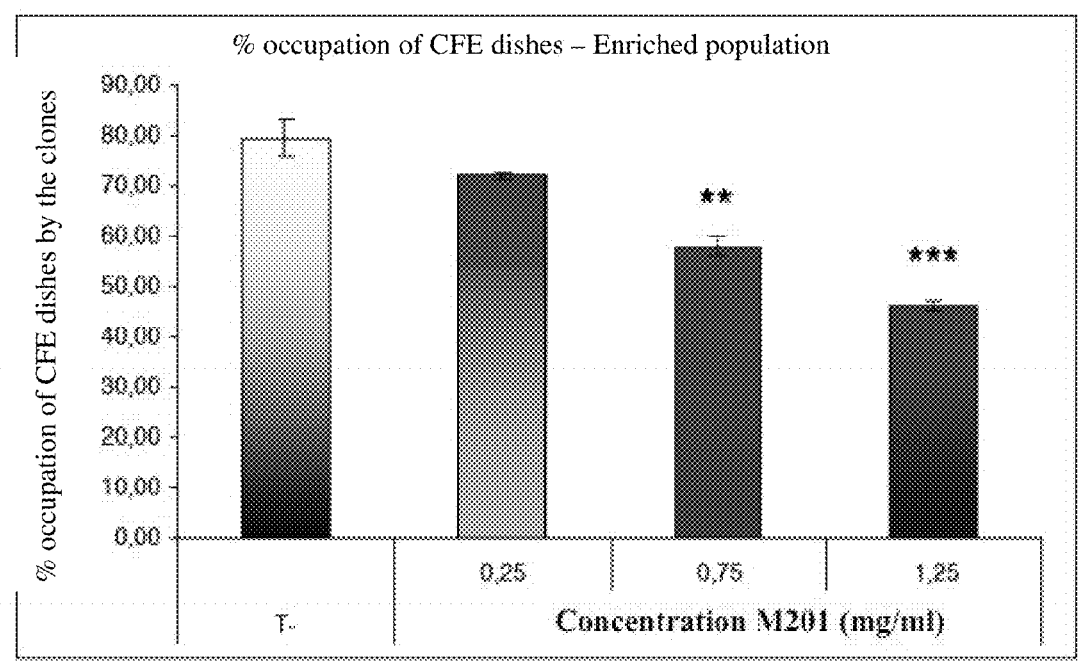
FIG. 1: Determination of the percentage occupation of the CFE dishes by the clones after fixing and staining of the clones obtained after 13 days of culture, using the "Image J" software, for the population enriched in stem cells. The results are the means of the triplicates per condition.

On the other hand, the percentage occupation of the CFE dishes by the clones after 13 days of culture is significantly different between the control condition and the Hemarina-M201 at 0.25 mg/ml, Hemarina-M201 at 0.75 mg/ml and Hemarina-M201 at 1.25 mg/ml conditions: it is lower for the conditions with Hemarina-M201, in a dose-dependent manner (FIG. 1). The higher the concentration of Hemarina-M201, the lower this percentage occupation of the CFE dishes.

Hemarina-M201 therefore influences cell differentiation. The number of viable clones in the presence of Hemarina-M201 is the same at the various times as at time T0, but, in the absence of Hemarina-M201, the cells have differentiated, as shown by the area of occupation of the dishes, which increases.

The results obtained with the other bank are similar to those obtained with the first bank.

In conclusion, whatever the cell bank studied, the number of cell clones obtained does not appear to drastically change given the standard deviations.

These results indicate that the Hemarina-M201 hemoglobin prevents cell differentiation of the stem cells of run-of-the-mill keratinocytes derived from the banks, while at the same time preserving their viability.

Evaluation of Hemarina-M201 on Populations of Freshly Extracted Keratinocytes Enriched in or Depleted of Stem Cells and Progenitor Cells:

Population Enriched in Stem Cells and Progenitor Cells:

The percentage occupation of the CFE dishes by the clones after 13 days of culture is significantly lower for the Hemarina-M201 at 0.75 mg/ml and Hemarina-M201 at 1.25 mg/ml conditions, compared with the control and with Hemarina-M201 at 0.25 mg/ml.

Run-of-the-Mill Population of Freshly Isolated Keratinocytes:

The number of clones present in the CFE dishes after 13 days of culture is not significantly different between the control, Hemarina-M201 at 0.25 mg/ml and Hemarina-M201 at 0.75 mg/ml conditions, but is significantly higher than the Hemarina-M201 at 1.25 mg/ml condition.

The percentage occupation of the CFE dishes by the clones after 13 days of culture is significantly lower for the Hemarina-M201 at 0.25, 0.75 and 1.25 mg/ml conditions, in a dose-dependent manner, compared with the control.

Population Depleted of Stem Cells and Progenitor Cells:

The number of clones present in the CFE dishes after 13 days of culture is not significantly different between the control and Hemarina-M201 at 0.25 mg/ml conditions. On the other hand, the Hemarina-M201 at 0.75 and 1.25 mg/ml conditions have significantly lower numbers of clones, in a dose-dependent manner.

The percentage occupation of the CFE dishes by the clones after 13 days of culture is significantly lower for the Hemarina-M201 at 0.25, 0.75 and 1.25 mg/ml conditions, in a dose-dependent manner, compared with the control.

In conclusion, whatever the cell population studied (run-of-the-mill population, or population enriched in or depleted of stem cells and progenitor cells), the Hemarina-M201 hemoglobin blocks the differentiation potential of the stem cells giving keratinocytes. The number of clones does not change in the presence of Hemarina-M201 and their viability remains intact.

CONCLUSION

These studies show that the Hemarina-M201 hemoglobin has an action on the clonogenic potential of the cell populations tested. Hemarina-M201 prevents the differentiation of the stem cells, while at the same time preserving their viability.

The invention claimed is:
1. A method for maintaining stem cells in an undifferentiated state, comprising a step of mixing said stem cells with at least one extracellular hemoglobin, globin or globin protomer from annelids in amount sufficient to maintain the stem cells in an undifferentiated state,
   wherein the stem cells are animal progenitor cells or animal mesenchymal stem cells, and
   said annelids are from the family Nereididae.
2. The method of claim 1, wherein the extracellular hemoglobin, globin or globin protomer is present in a composition comprising a buffer solution.
3. The method of claim 1, wherein the annelid is *Nereis* sp.
4. The method of claim 1, wherein the annelid is *Nereis virens*.
5. The method of claim 2, wherein the extracellular hemoglobin, globin or globin protomer is present in the composition at a concentration of between 0.001 and 10 mg/ml.
6. The method of claim 1, wherein the stem cells are human stem cells.
7. A method for preserving stem cells in the undifferentiated state, comprising a step of mixing said stem cells with a buffer solution comprising at least one extracellular hemoglobin, globin or globin protomer from annelids in amount sufficient to preserve the stem cells in an undifferentiated state,
   wherein the stem cells are animal progenitor cells or animal mesenchymal stem cells, and
   said annelids are from the family Nereididae.
8. The method of claim 7, wherein the buffer solution comprises sodium chloride, calcium chloride, magnesium chloride, potassium chloride, sodium gluconate and sodium acetate, and has a pH of between 6.5 and 7.6.
9. The method of claim 2, wherein the buffer solution comprises sodium chloride, calcium chloride, magnesium chloride, potassium chloride, sodium gluconate and sodium acetate, and has a pH of between 6.5 and 7.6.
10. The method of claim 2, wherein the extracellular hemoglobin, globin or globin protomer is present in the composition at a concentration of between 0.20 and 1.50 mg/ml.
11. The method of claim 8, wherein the buffer solution has a pH of $7.1 \pm 0.5$.
12. The method of claim 1, wherein the stem cells are epidermal progenitor cells.
13. The method of claim 1, wherein the stem cells are maintained in an undifferentiated state for at least 13 days.
14. The method of claim 1, comprising mixing the stem cells with the at least one extracellular hemoglobin, globin or globin protomer from annelids, and maintaining the stem cells in an undifferentiated state while the stem cells are cultured in vitro.

15. A method for maintaining stem cells in an undifferentiated state, comprising a step of mixing said stem cells with at least one extracellular hemoglobin, globin or globin protomer from annelids in amount sufficient to maintain the stem cells in an undifferentiated state,
 wherein the stem cells are epidermal progenitor cells, and said annelids are from the family Nereididae.

16. The method of claim 1, wherein the stem cells are epidermal progenitor cells or mesenchymal stem cells.

17. The method of claim 1, wherein the stem cells are mesenchymal stem cells.

* * * * *